United States Patent
Hooft et al.

(10) Patent No.: US 6,251,060 B1
(45) Date of Patent: Jun. 26, 2001

(54) APPARATUS AND METHOD FOR TEMPORARILY INSERTING A RADIOACTIVE SOURCE IN AN ANIMAL BODY

(75) Inventors: Eric Van't Hooft, Brasschaat (BE); Hans Martin Schot, Veenendaal (NL); Albert Dirk Adrianus Koster, Utrecht (NL); Lu Anne Johnson, Zeist (NL)

(73) Assignee: Nucletron B.V., Veenendaal (NL)

( * ) Notice: Subject to any disclaimer, the term of this patent is extended or adjusted under 35 U.S.C. 154(b) by 0 days.

(21) Appl. No.: 09/375,526

(22) Filed: Aug. 17, 1999

(30) Foreign Application Priority Data

Jul. 23, 1999 (NL) ....................................... 1012698

(51) Int. Cl.⁷ ....................................... A61N 5/00
(52) U.S. Cl. .................................................. 600/3
(58) Field of Search ................. 604/48, 502, 506, 604/93.01, 158, 164.01, 171, 264; 600/1, 3, 7, 8

(56) References Cited

U.S. PATENT DOCUMENTS

| 4,327,722 | * | 5/1982 | Groshong et al. | 604/510 |
| 4,431,426 | * | 2/1984 | Groshong et al. | 604/158 X |
| 4,529,399 | * | 7/1985 | Groshong et al. | 604/510 |
| 4,697,575 | * | 10/1987 | Horowitz | 600/8 |
| 4,763,671 | * | 8/1988 | Goffinet | 600/7 X |
| 5,259,847 | * | 11/1993 | Trambert | 604/264 X |
| 5,391,139 | * | 2/1995 | Edmundson | 600/7 |
| 5,524,644 | | 6/1996 | Crook . | |
| 5,814,073 | | 9/1998 | Bonutti . | |
| 5,860,909 | * | 1/1999 | Mick et al. | 600/7 |
| 6,030,333 | * | 2/2000 | Sioshansi et al. | 600/3 |
| 6,036,632 | * | 3/2000 | Whitmore, III et al. | 600/7 |

FOREIGN PATENT DOCUMENTS

| D. 2736318 | 2/1979 | (DE) . |
| 788833 | 1/1958 | (GB) . |
| 9302140 | 7/1995 | (NL) . |
| WO 9622123 | 7/1996 | (WO) . |

* cited by examiner

Primary Examiner—John P. Lacyk
Assistant Examiner—Joseph A. Cadugan
(74) Attorney, Agent, or Firm—Birch, Stewart, Kolasch & Birch, LLP

(57) ABSTRACT

A method and apparatus for temporarily inserting a radioactive source in a body. A flexible, closed-end sheath is first inserted in the body in a known way. Thereafter a radiation device having a radioactive source therein is inserted into the sheath and detachably connected to a fixing element. After a predetermined period of time, the radiation device is disconnected from the fixing element and removed from the body.

24 Claims, 9 Drawing Sheets

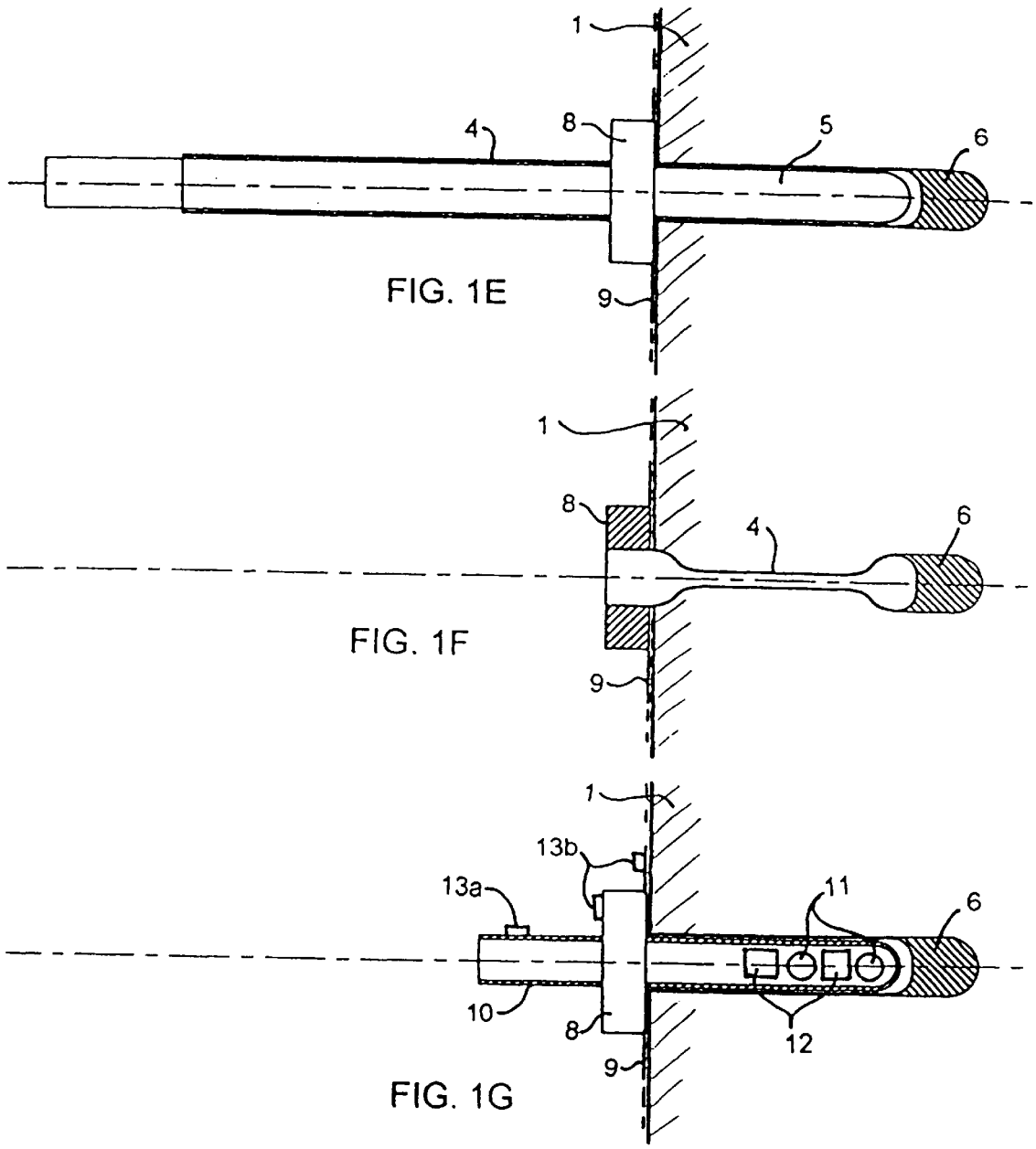

APPARATUS AND METHOD FOR TEMPORARILY INSERTING A RADIOACTIVE SOURCE IN AN ANIMAL BODY

The invention relates to a method for temporarily inserting at least one radioactive source in an animal body comprising providing a channel in said body by means of a hollow open needle, inserting a flexible closed end sheath in the hollow open needle, retracting the hollow open needle over the flexible closed end sheath while maintaining the flexible closed end sheath in position in the channel in the body, fixing the flexible closed end sheath relative to the body by means of a fixing element, inserting into the sheath a radiation device having at least one radioactive source and after a period of time retracting the radiation device from the flexible closed end sheath.

The invention also relates to an apparatus for temporarily inserting at least one radioactive source in an animal body comprising a hollow open needle for providing a channel into the body, a flexible closed end sheath for insertion into the channel through the hollow open needle, the hollow open needle being retractable over the flexible closed end sheath, a fixing element for fixing the flexible closed end sheath relative to said body, a radiation device insertable into the flexible closed end sheath, the radiation device having at least one radioactive source therein.

BACKGROUND OF THE INVENTION

In the process of brachytherapy a radioactive source is brought to the vicinity of cancerous tissue for irradiating that cancerous tissue with radioactive radiation. Numerous proposals have been made for devices to carry out such processes. Such processes are e.g. known as manual low dose rate brachytherapy using wires, seeds, pellets, tubes and high dose rate or remote afterloading HDR brachytherapy. In LDR and HDR brachytherapy one or more low and high, respectively, intensity radioactive sources are fixed at a distal end of a so-called guide wire, i.e. remote afterloading. For certain types of cancer e.g. prostate cancer or breast cancer, more than one time spaced apart dose of radiation is required to be effective. Those doses are given over a period of several days. A patient has to be hospitalized during that period. Each time a dose is to be delivered during that period needles are placed into the body of the patient and treatment started. It is also known to have the needles remain in the body. Especially HDR brachytherapy needs only a few minutes or less for one dose. Thus for a patient such method means a long time in the hospital for a few short time treatments. Patients perceive such a method as being quite burdensome.

It is known in brachytherapy to insert a number of needles in a body semi-permanently for the total duration of the treatment. In that case a number of needles is inserted into the body, usually by means of a template, and fixed relative to the body by means of a fixing element. The template may also function as a fixing element. Each of the needles then is provided with a coupling. All needles stick out of the body for a certain distance and are provided with a coupling. Through the couplings so-called guide tubes or transfer tubes can be connected to the needles. As is well known in brachytherapy a so-called afterloader machine may be used to control the transport of the radiation source from the machine to the needles through the guide tubes or transfer tubes. An afterloader machine therefore is provided with an indexer device. The guide tubes or transfer tubes with ends thereof coupled to the fixing element are in turn coupled at opposite ends to the indexer. As is well known from afterloader brachytherapy machines manufactured and sold by e.g. Nucletron B.V. from the Netherlands a radioactive source at a distal tip of a so-called guide wire is transported under control of the machine from a safe in the machine through the indexer into a guide tube and through the guide tube into a corresponding needle. After a certain period the guide wire with the radioactive source is retracted into the afterloader machine. In case a further irradiation is to take place from another needle, the indexer is controlled such that a further guide tube is connected to receive the guide wire with the radioactive source at the tip. And so on until all required irradiations have taken place from the various needles. Then the needles are disconnected from the guide tubes. The patient then is "free" to walk around with a set of needles in his or her body until the next treatment has to take place. It is known to use plastic needles that have a small amount of flexibility instead of inflexible metal needles. The above description relates also to such flexible plastic needles.

During the periods that no treatment is taking place the patient is free in theory to walk around, however, in practice the set of needles sticking out of the body prevents the patient to feel really free. In any case it is not possible for such a patient to leave the hospital and return only for a next treatment.

BRIEF DESCRIPTION OF THE INVENTION

An object of the invention is to provide a method for temporarily inserting at least one radioactive source in a body by use of a radiation device which comprises a hollow closed end needle, said hollow closed end needle being provided with at least one radioactive source in it. The hollow closed end needle is inserted into a flexible closed end sheath, in which the hollow closed end needle is detachably connected to a fixing element and in which after a period of time the hollow closed end needle is disconnected from the fixing element and removed from the flexible closed end sheath.

A further object of the invention is to provide a method in which said at least one radioactive element is semi-permanently positioned in said hollow closed end needle.

A further object of the invention is to provide an apparatus for temporarily inserting at least one radioactive source in an animal body comprising a hollow open needle for defining a channel into the body, a flexible closed end sheath for insertion into the channel through the hollow open needle, the hollow open needle being retractable over the flexible closed end sheath. A fixing element is provided for fixing the flexible closed end sheath relative to the body. A radiation device is insertable into the flexible closed end sheath. The radiation device comprises at least one radioactive source and a hollow closed end needle. At least one radioactive source is positionable inside the hollow closed end needle and means are present for detachably connecting the needle to the fixing element.

A further object of the invention is to provide such a system in which the at least one radioactive element is semi-permanently positioned in the hollow closed end needle.

Thereby it is achieved that for a single patient a set of needles with radioactive sources is available for more than one treatment in which the radioactive sources are positioned in the needles in the configuration for that particular patient. The needles with the radioactive sources in them can then be stored until the next treatment takes place.

A further object of the invention is for the fixing element to comprise a breathable tape that is adhereable to the body.

A still further object of the invention is that the flexible closed end sheath is collapsible under pressures present in the channel in the body.

A still further object of the invention is to provide a part near or at a distal end of the flexible closed end sheath that is not collapsible under pressures present in the channel in said body.

Thereby it is achieved that the non-collapsible part acts as an anchoring device for the closed end sheath in the body.

A still further object of the invention is that a radiopaque marker is present in a distal end of the flexible closed end sheath.

It is a still further object of the invention to provide the hollow closed end needle with a coupling device slideable along the hollow closed end needle for fixing the needle to the fixing element.

It is a further object of the invention to provide a coupling device as fastenable upon said hollow closed end needle.

Thereby it is achieved that the hollow closed end needles can be used without any further device such as an afterloader machine being needed to transport at least one radioactive element from the afterloader machine into the hollow closed end needle. Moreover it is very convenient for making use of the hollow closed end needles as storage for the at least one radioactive source in the periods between treatments.

It is a further object of the invention to provide a button with a flange part attachable to the tape.

It is a still further object of the invention to provide a flexible closed end sheath of heat meltable material which upon cooling in contact with said button fixedly connects to said button.

Thereby it is achieved that said buttons are the only elements that stick out. Such sticking out is thereby reduced to less than a few millimeter.

It is a further object of the invention to provide the hollow closed end needle and the button or the tape with identification means.

Thereby it is achieved that stored needles can easily be inserted into the closed end sheaths without being switched, thereby providing security that a needle is replaced in its correct location relative to the body and the cancerous tissue.

Further details, advantages and features of the invention are shown not only in the claims and the features therein, singly and/or in combination, but also in the following description of preferred embodiments shown in the drawing.

BRIEF DESCRIPTION OF THE DRAWINGS

In the drawing,

FIGS. 1A through 1G show schematically the method according to the invention;

DESCRIPTION OF PREFERRED EMBODIMENTS

Figure 1A:
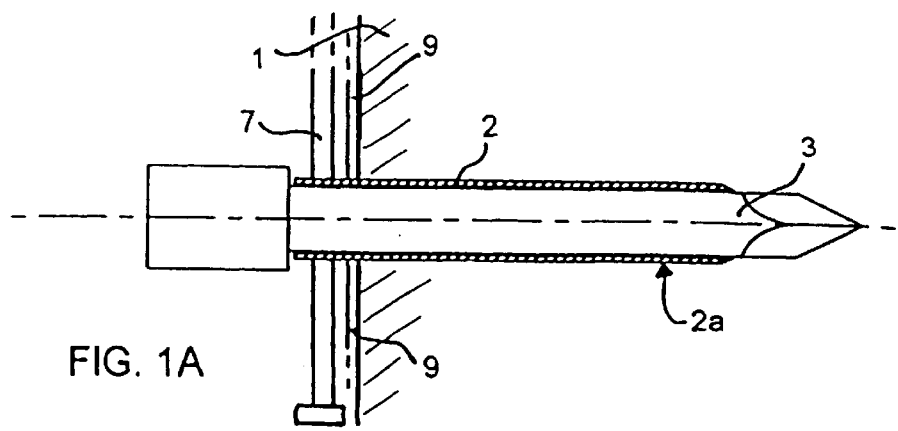
Figure 1B:
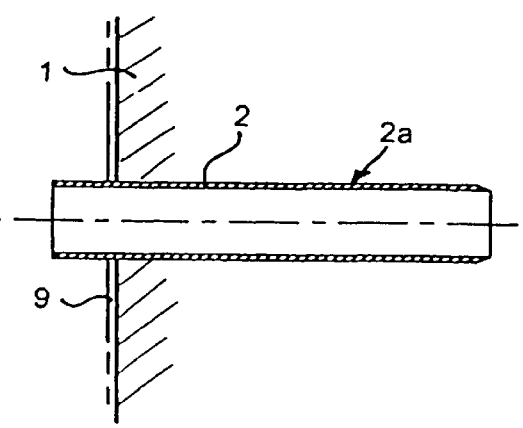
Figure 1C:
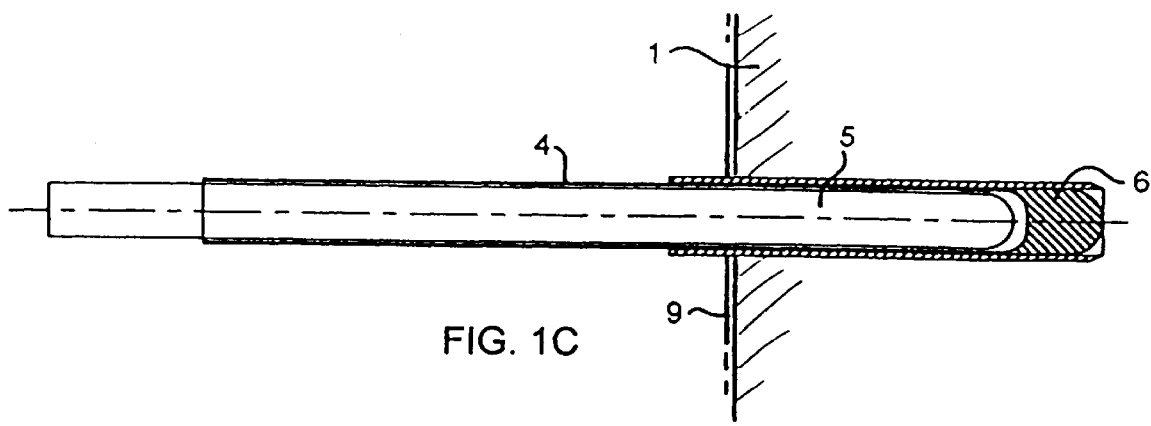
Figure 1D:
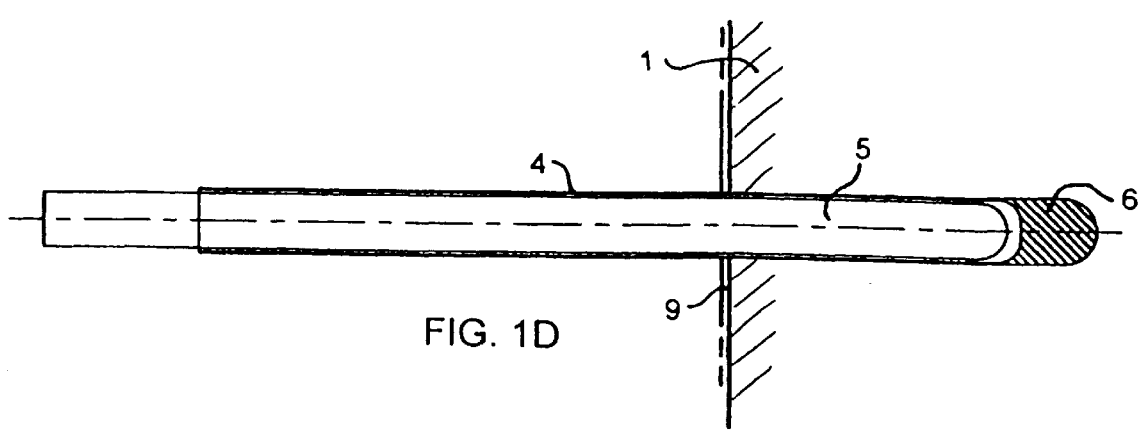

In FIGS. 1A through 1G a body is indicated by numeral 1. At the location on the body where needles are to be inserted a flexible breathable tape 9 is attached to the body. In a well known way using e.g. a template 7 or making use of indications on the breathable tape 9 an open needle 2 with a trocar needle 3 inside it is inserted into the body 1 near a cancerous tissue (not shown). The trocar needle 3 fills up the open needle 2 so that during insertion into the body a channel, generally 2a, is formed. Subsequently the trocar needle 3 is retracted. The open needle 2 retains the channel, generally 2a, as shown in FIG. 1B. Next a flexible closed end sheath 4 with a distal tip 6 is inserted into the open needle 2 with the help of an obturator 5. The obturator 5 prevents the sheath 5 from being moved and from collapsing under pressures present on the channel when the support given by the needle 2 is not maintained any more. The support given by needle 2 is not there anymore after removal of the needle 2 and after insertion of the sheath 4 with the obturator 5. The situation that is created after needle 2 has been removed is shown in FIG. 1D. Next a button 8 (see FIG. 1E) is shifted over the flexible closed end sheath 4. The button 8 is attached to the breathable tape 9. Thereafter obturator 5 is withdrawn and flexible closed end sheath 4 is cut off at the button 8 as shown in FIG. 1F. Subsequently the button 8 and the flexible closed end sheath 4 are connected together for example by gluing. In a preferred embodiment however flexible closed end sheath 4 is made of a heat meltable plastic material which material when being in a heat melted state upon cooling in contact with button 8 fixedly connects to button 8. Also shown in FIG. 1F is flexible closed end sheath 4 in a collapsed state after withdrawal of obturator 5. Flexible closed end sheath 4 is so flexible that it collapses under the pressures present in the channel made by needle 2 after its withdrawal and after withdrawal of obturator 5. Also shown in FIG. 1F is a way of anchoring flexible closed end sheath 4. In the embodiment shown in FIG. 1F distal tip 6 is less flexible than the remainder of flexible closed end sheath 4. As a consequence distal tip 6 does not, at least fully, collapse under the pressures present on the channel made by needle 2. Since the remainder of flexible closed end sheath 4 has collapsed and tip 6 has not, at least fully, collapsed the respective cross sections are different and it is not possible for flexible closed end sheath 4 to move, i.e. distal tip 6 acts as an anchor for anchoring flexible closed end sheath 4 in the body 1. Tip 6 may not only be less flexible than the remainder of flexible closed end sheath 4, but it may also comprise a radiopaque material. Thereby it is possible under fluoroscopy to determine the locations of various flexible closed end sheaths 4 in a body. After the flexible closed end sheath 4 has been fixed inside the body and the button 8 attached to tape 9 a hollow closed end needle 10 is inserted into the flexible closed end sheath 4. Inside hollow closed end needle 10 a number of radioactive pellets 11, if necessary, separated by non-radioactive spacers 12 is present. In a way to be described hereinafter the needle 10 is detachably connected to button 8.

After hollow closed end needle 10 has been in place for a time as desired it is retracted and may be stored with the radioactive pellets and the non radioactive spacers inside it until the next treatment of the same patient. In order that the same needle is inserted into the same flexible closed end sheath at the next time for treatment, an indicator 13a may be attached to the hollow closed end needle 10 and a corresponding indicator 13b may be attached to the button 8 and/or the breathable tape 9.

Figure 2:
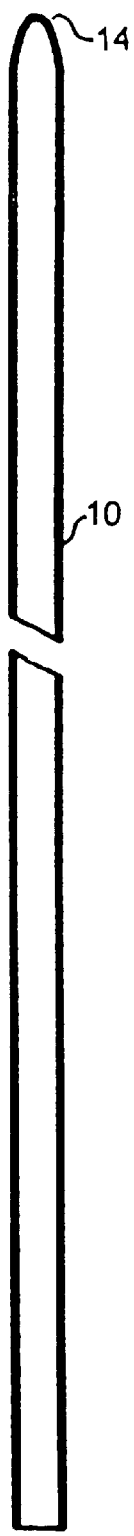
FIG. 2 shows a needle for use in a system according to the invention.

FIG. 2 shows a longitudinal section through hollow closed end needle 10; preferably but not necessarily a tip 14 is cone pointed.

Figure 3:
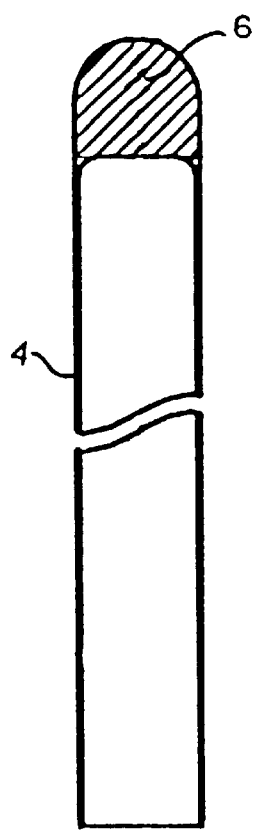
FIG. 3 shows a first embodiment of a flexible closed end sheath for use in a system according to the invention.
Figure 4:
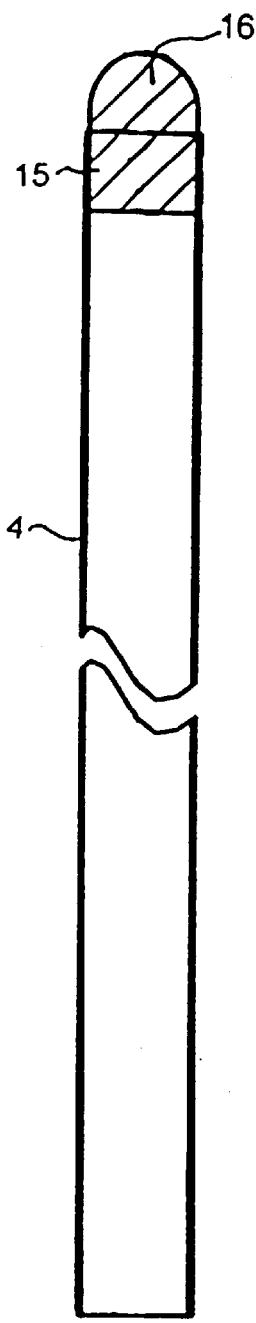
FIG. 4 shows a second embodiment of a flexible closed end sheath for use in a system according to the invention.

An example of a flexible closed end sheath is shown in FIG. 3. The outer diameter of it may be about 1.5 mm and its wall thickness may be 0.05 mm. It may be made of a flexible plastic such as Pebax 7033. Tip 6 is of a length of about 2 mm and is made of Pebax 7033. Since tip 6 is fully filled with material it is not, at least fully, collapsible whereas the remainder of flexible closed end sheath 4 is collapsible at least under the pressures present on a 1.5 mm channel in a body. In a preferred embodiment the Pebax 7033 material is mixed with about 25% barium sulfate. Barium sulfate is much less X-ray transparent than pebax 7033. As a consequence tip 6 which is fully filled shows up under fluoroscopy whereas the remainder of flexible closed end sheath 4 does not. Another embodiment of a tip that is visible under fluoroscopy is shown in FIG. 4. Tip 14 is made of polyvinylchloride mixed with 60% barium sulfate and is a separate item that is sealed to flexible sheath 4 at 15.

FIGS. 5A through 7B show various ways in which buttons 8 may be connected to flexible closed end sheaths 4. Flexible closed end sheath 4 is made of a plastic such as pebax 7033 that melts when heated. Upon cooling and when in contact then with a button 8 the melted plastic of flexible sheath 4 connect strongly to the button.

Figure 5A:
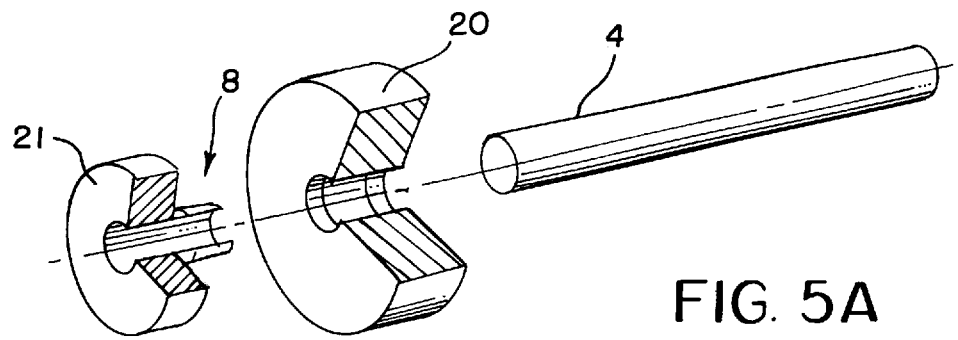
FIGS. 5A and 5B show a first embodiment of connecting a button to a flexible closed end sheath.
Figure 5B:
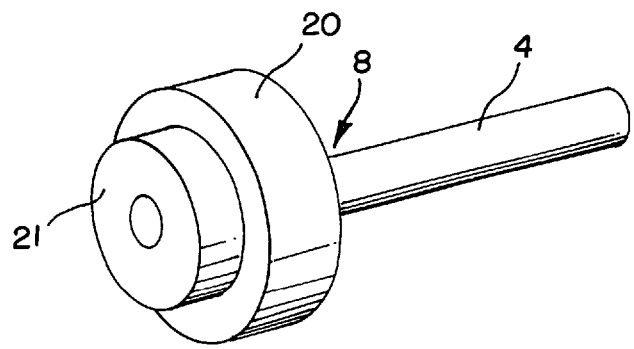

In the embodiment shown in FIGS. 5A and 5B button 8 comprises two parts 20 and 21. To make a connection between flexible closed end sheath 4 and button 8 element 20 is slid over the flexible closed end sheath 4 until it adheres to a skin surface of the body 1 or to breathable tape 9. Then flexible sheath 4 is cut to length at a base of element 20. Next insert piece 21 is slid under flexible closed end sheath 4 and snaps to element 20.

Figure 6A:
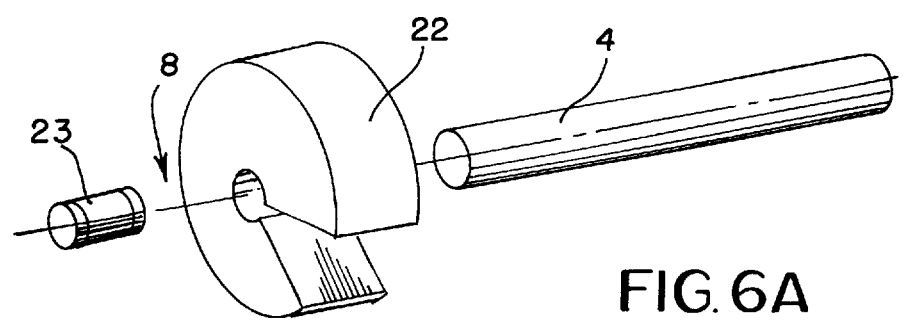
FIGS. 6A and 6B show a second embodiment of connecting a button to a flexible closed end sheath.
Figure 6B:
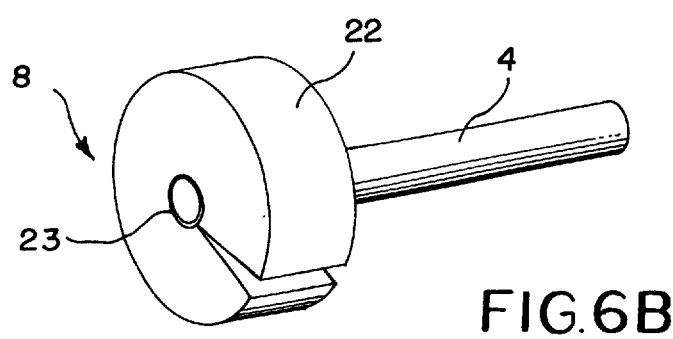

In the embodiment shown in FIGS. 6A and 6B button 8 comprises an element 22 and a cylinder 23. To make a connection between flexible closed end sheath 4 and button 8 element 22 is slid over the flexible closed end sheath 4 until it adheres to a skin surface of the body 1 or to breathable tape 9. Then flexible sheath 4 is cut to length at a base of element 22. Subsequently an obturator (not shown) is inserted into the flexible closed end sheath 4 (unless obturator 5 had not been withdrawn yet). Next cylinder 23 is slid over the obturator and into the flexible closed end sheath 4. The inside diameter of element 22 is made smaller to tighten and fix the flexible closed end sheath 4 in place between the inside of the element 22 and cylinder 23.

Figure 7A:
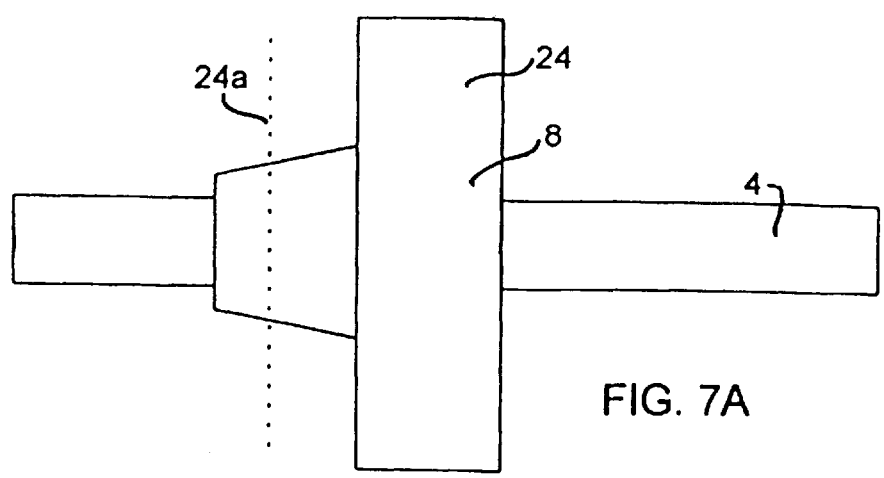
FIGS. 7A and 7B show a third embodiment of connecting a button to a flexible closed end-sheath.
Figure 7B:
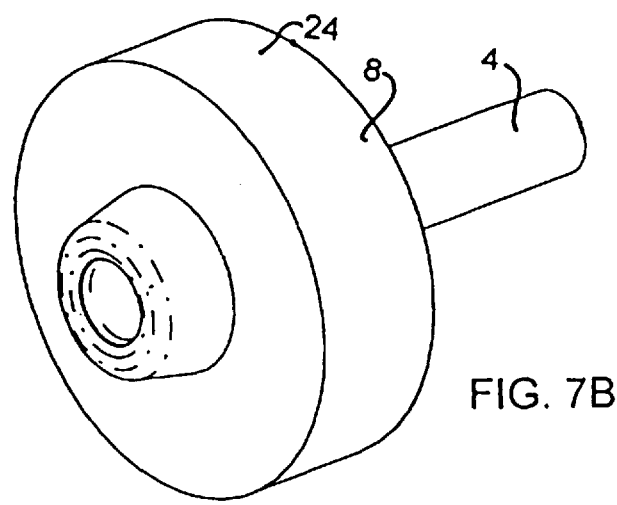

In the embodiment shown in FIGS. 7A and 7B button 8 comprises an element 24. Suitable materials for element 24 are known as PA 6 and PA 12. To make a connection between flexible closed end sheath 4 and element 24 the latter is slid over the flexible closed end sheath 4 until it adheres to a skin surface of the body 1 or to breathable tape 9. Then flexible sheath 4 and element 24 are cut to length as shown by dotted line 24a. Cutting to length may be done easily by using a so-called cautery, a medical instrument used for making incisions with a thin heatable wire at a tip. If the opening after cautery is too small for the needle 10 to pass the opening may be widened with a hot metal point like a soldering point.

FIGS. 8A through 10B show various ways in which a hollow closed end needle 10 may be detachably connected to a button that is fixed to a flexible closed end sheath 4.

Figure 8A:
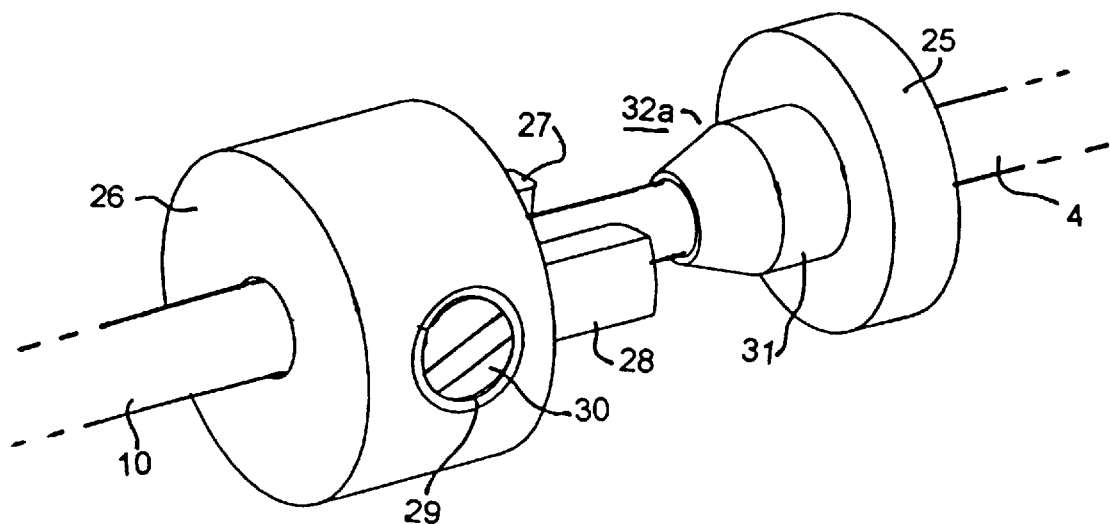
FIGS. 8A and 8B show a first embodiment of connecting a needle/fastening stopper to a button.
Figure 8B:
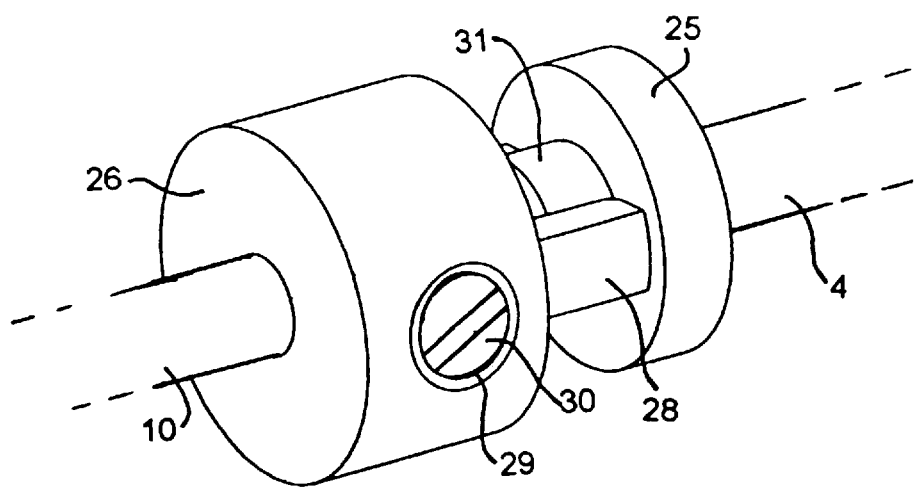

In the embodiment shown in FIGS. 8A and 8B a button 25 comparable to element 24 is fixedly connected to a flexible closed end sheath 4. A hollow closed end needle 10 has been inserted in flexible closed end sheath 4. Slideable over hollow closed end needle 10 is a fastenable stopper 26. Stopper 26 comprises two teeth 27 and 28. Stopper 26 further is provided with a threaded opening 29 for a nut 30. Once hollow closed end needle 10 has been inserted into place in flexible closed end sheath 4 stopper 26 is slid over hollow closed end needle 10 in the direction of button 25 until teeth 27 and 28 grip around cylindrical surface 31 of element 32a of button 25. The diameter of surface 31 is slightly larger than the distance between teeth 27 and 28. As a consequence stopper 26 may be pushed with its teeth 27 and 28 over surface 31 and can not thereafter be loosened therefrom without applying force. After stopper has been brought into position with its teeth 27 and 28 around surface 31 nut 30 is tightened such that stopper 26 and hollow closed end needle 10 are fixedly connected. In order to remove hollow closed end needle 10 force is applied to remove stopper 26 with its teeth 27 and 28 from surface 31. Concurrently therewith hollow closed end needle 10 is moved out of flexible closed end sheath 4. Stopper 26 may remain in place so that at a next treatment hollow closed end needle only has to be pushed in so far that teeth 27 and 28 grip around surface 31.

Figure 9A:
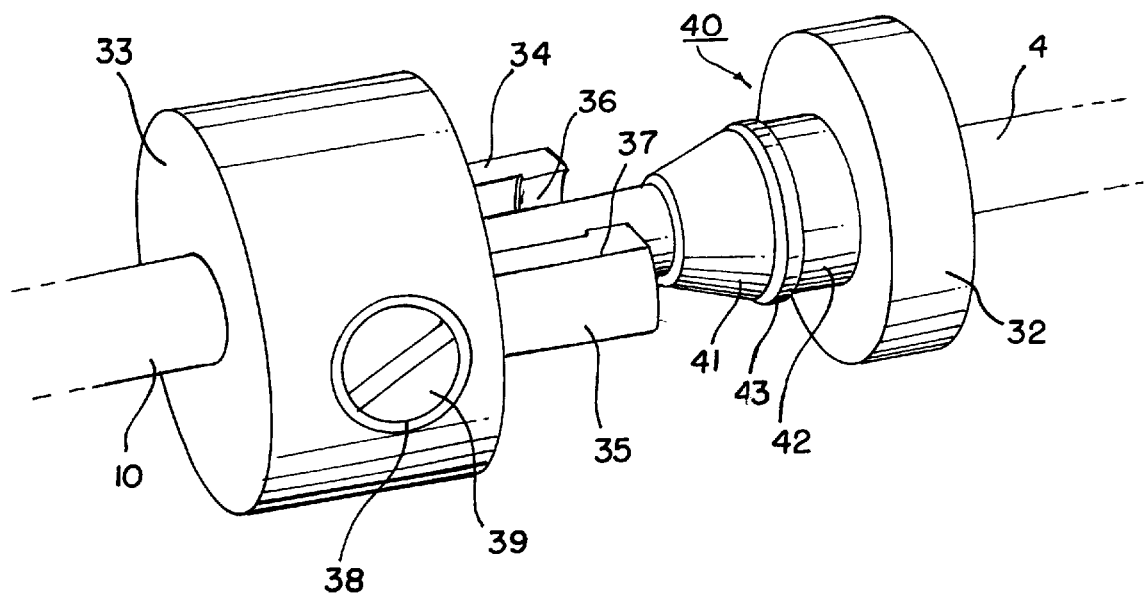
FIGS. 9A and 9B show a second embodiment of connecting a needle/fastening stopper to a button.
Figure 9B:
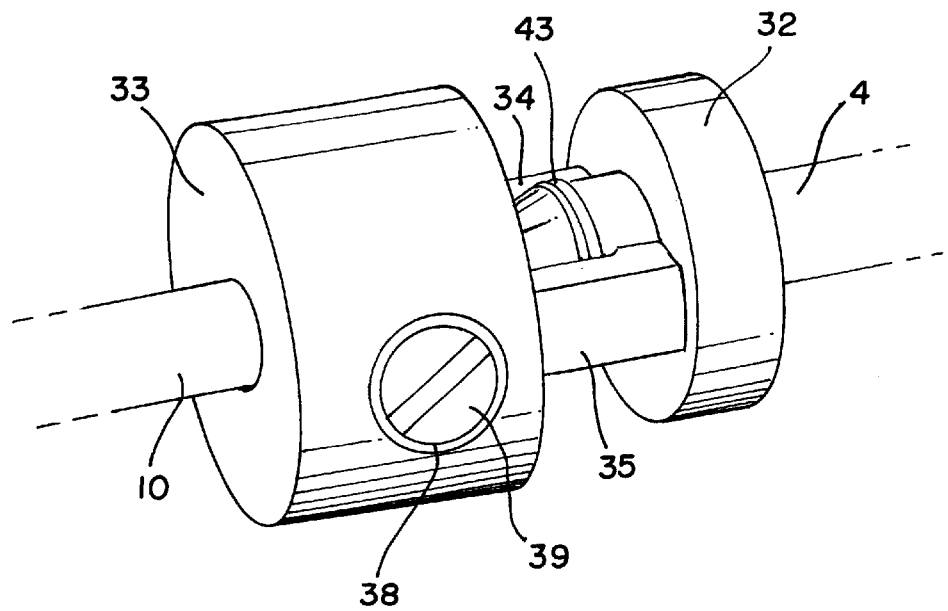

In the embodiment shown in the FIGS. 9A and 9B a button 32 comparable to element 24 is fixedly connected to a flexible closed end sheath 4. A hollow closed end needle 10 has been inserted in flexible closed end sheath 4. Slideable over hollow closed end needle 10 is a fastenable stopper 33. Stopper 33 comprises two teeth 34 and 35. Teeth 34 and 35 have raised portions 36 and 37, respectively. Stopper 33 further is provided with a threaded opening 38 for a nut 39. Button 32 is provided with a conical-cylindrical part 40 including a conical part 41, a cylindrical part 42 and a ring-like part 43 with a diameter larger than the diameter of cylindrical part 42. The diameter of ring-like part 43 is about equal to the distance between teeth 34 and 35, however, larger than the distance between the raised portions 36 and 37. The diameter of the cylindrical part 42 is about equal to the distance between the raised portions 36 and 37. Once hollow closed end needle 10 has been inserted into place in flexible closed end sheath 4 stopper 33 is slid over hollow closed end needle 10 in the direction of button 32 until teeth 34 and 35 with their raised portions 36 and 37 grip around ring-like part 43 of element 40 of button 32. Then nut 39 is turned to fixed stopper 33 relative to hollow closed end needle 10. In order to disconnect hollow closed end needle 10 from button 32 force has to be applied to overcome the form-fix formed by teeth 34 and 35 with raised portions 36 and 37 together with ring-like part 43.

Figure 10A:
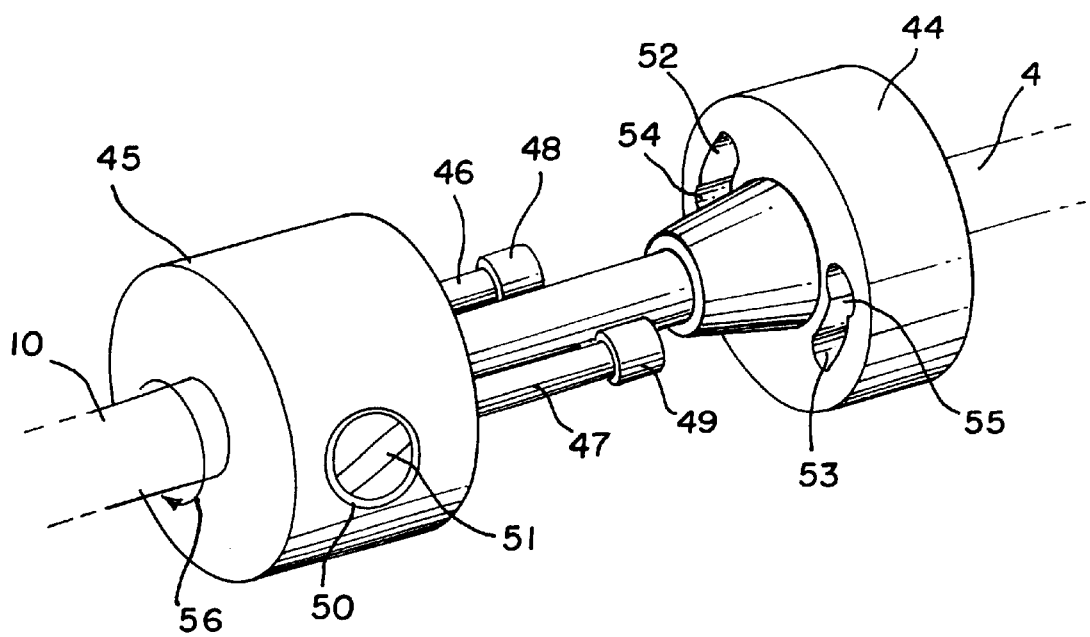
FIGS. 10A and 10B show a third embodiment of connecting a needle/fastening stopper to a button.
Figure 10B:
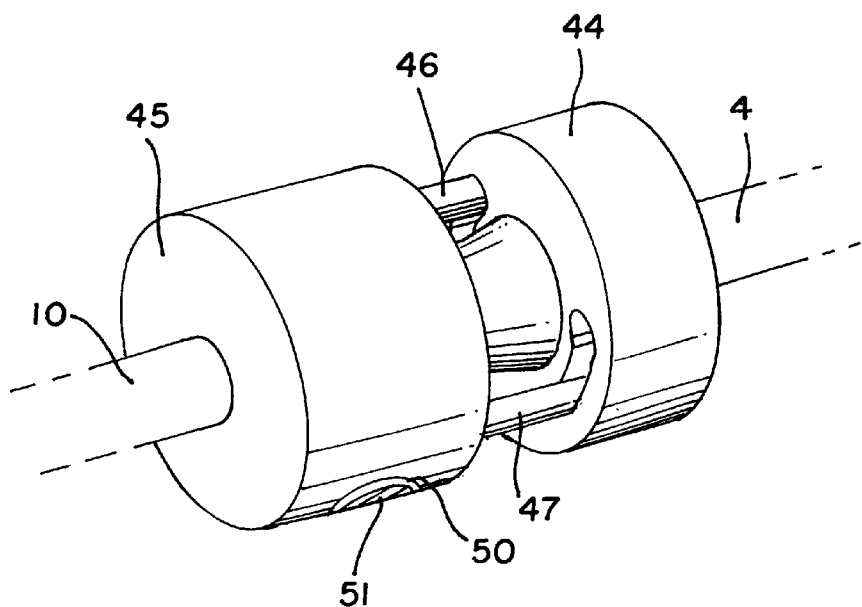

In the embodiment shown in the FIGS. 10A and 10B a button 44 comparable to button 24 is fixedly connected to a flexible closed end sheath 4. A hollow closed end needle 10 has been inserted in flexible closed end sheath 4. Slideable over hollow closed end needle 10 is a fastenable stopper 45. Stopper 45 comprises two cylindrical teeth 46 and 47 provided with flanges 48 and 49 respectively. Stopper 45 further is provided with a threaded opening 50 for a nut 51. Button 44 is provided with two slots 52 and 53, each having a small part 54 and 55 respectively of larger size and a remainder part of smaller size. The flanges 48 and 49 fit through the parts 54 and 55 of larger size but not through the remainder part of smaller size. The cylindrical teeth 46 and 47 fit through the remainder parts of openings 52 and 53 also. Further down button 44 the smaller size parts of openings 52 and 53 have sufficiently sized dimensions to accommodate the flanges 48 and 49. Once hollow closed end needle 10 has been inserted into place in flexible closed end sheath 4 stopper 45 is slid over hollow closed end needle 10 in the direction of button 44 until teeth 46 and 47 with their flanges 48 and 49 enter into openings 54 and 55. That movement is continued until flanges 48 and 49 will not perceive any resistance anymore when stopper 45 is turned in the direction of arrow 56. Thereby the flanges 48 and 49 lock the stopper 45 since after rotation in the direction of arrow 56 flanges 48 and 49 cannot be removed from stopper 45 anymore. Teeth 46 and 47 with flanges 48 and 49 operate like a key in a lock, the lock being formed by the openings 52 and 53. In order to unlock stopper 45 it is simply turned counter the direction of arrow 56 after which it can be retracted together with the hollow closed end needle 10.

Figure 11:
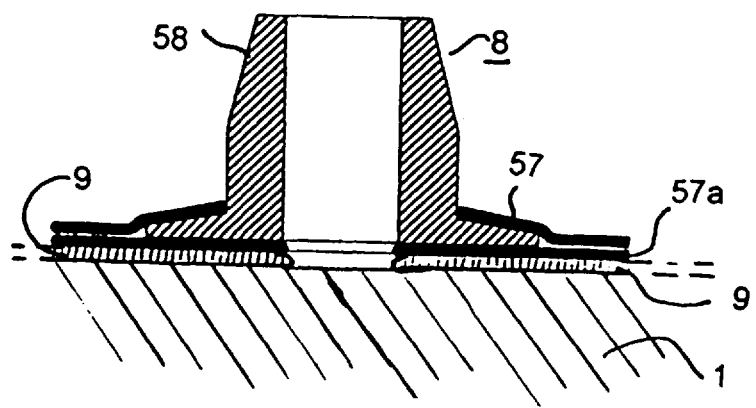
FIG. 11 shows an embodiment of adhering a button to a breathable tape.

FIG. 11 shows a preferred embodiment for fixing a button 8 to a breathable tape 9. Referring to FIGS. 7A through 9B one may understand that a cylindrical part of the buttons 24, 25 and 32 shown therein may be made rather thin as shown in cross section in FIG. 11 thereby forming a flange. An adhesive tape 57a is attached to the bottom of the button 8 and adheres to breathable tape 9. An adhesive tape 57 with an opening for the dome like structure 58 is slid over the dome like structure 58 and adheres to adhesive tape 57a. Thereby button 8 is fixedly connected to breathable tape 9.

Figure 12:
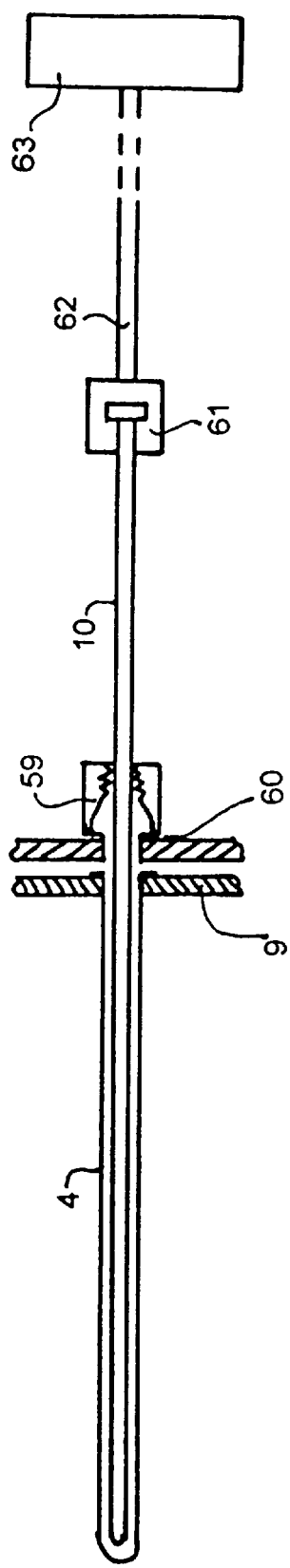
FIG. 12 shows an embodiment of the invention in which a hollow closed end needle is connected to an afterloader machine.

FIG. 12 shows an embodiment of the invention in which use can be made of an afterloader machine. Instead of buttons 8 clamps 59 are fixedly connected to breathable tape 9 through elements 60. A hollow closed end needle 10 is at its proximal end provided with a connector 61 for a guide tube 62 which is connectable to an afterloader machine 63. First needles 10 are inserted in the flexible closed end sheaths 4 and clamped through clamps 59. Next guide tubes 62 are connected to hollow closed end needles 10 through connectors 61. Subsequently the afterloader machine 63 is controlled in a well known way to push a wire with a radioactive element at its tip through guide tube 62 into hollow closed end needle 10 at a first position. After the radioactive element has resided for a certain period of time at said first position the wire is pushed a little further until the radioactive element at its tip reaches a second position in hollow closed end needle 10, etc. After a complete treatment the wire with the radioactive element at its tip is retracted in a known way and inserted into a second hollow closed end needle 10 etc. until all hollow closed end needles 10 have had their turn. Thereafter the connectors 61 are disconnected and the hollow closed end needles 10 detached from the clamps 59.

It should be noted that according to the abovementioned, various modifications may be obvious to a person skilled in the art. Such modifications are deemed to be within the scope of the invention.

What is claimed is:

1. Method for temporarily inserting at least one radioactive source in an animal body comprising inserting a hollow open needle into the body so as to provide a channel in the body, inserting a flexible closed end sheath in the hollow open needle, retracting the hollow open needle over the flexible closed end sheath and out of the body while maintaining the flexible closed end sheath in position in the channel in the body, fixing the flexible closed end sheath relative to the body, inserting into the sheath and the body a radiation device having at least one radioactive source therein, detachably connecting the radiation device to a fixing element and after a predetermined period of time disconnecting the radiation device from the fixing element and removing the radiation device from the flexible closed end sheath and the body.

2. Method according to claim 1, wherein the radiation device is a hollow closed end needle.

3. Method according to claim 2, wherein the at least one radioactive source is semi-permanently positioned in the hollow closed end needle.

4. An apparatus adapted to temporarily insert at least one radioactive source in an animal body, comprising a hollow open needle for inserting into a body so as to provide a channel in a body, a flexible closed end sheath for insertion into the hollow open needle, the hollow open needle being retractable from a body over the flexible closed end sheath, a fixing element for fixing the flexible closed end sheath relative to a body, a radiation device insertable into the flexible closed end sheath, and having at least one radioactive source therein, and a connecting element for detachably connecting the radioactive device relative to a body.

5. Apparatus according to claim 4 wherein the radiation device is a hollow closed end needle.

6. Apparatus according to claim 5 wherein the at least one radioactive source is semi-permanently positioned in the hollow closed end needle.

7. Apparatus according to claim 5, wherein the fixing element comprises a tape adhereable to a body.

8. Apparatus according to claim 7, wherein the tape is breathable tape.

9. Apparatus according to claim 7, wherein the fixing element has a button with a flange part and the flange part is attachable to the tape.

10. Apparatus according to claim 5, wherein a radiopaque marker is present in a distal end of the flexible closed end sheath.

11. Apparatus according to claim 5, wherein the connecting element has a clamping device for clamping the hollow closed end needle.

12. Apparatus according to claim 5, wherein the connecting element has a coupling device slideable along the hollow closed end needle.

13. Apparatus according to claim 12, wherein the coupling device is fastenable upon the hollow closed end needle.

14. Apparatus according to claim 13, wherein the coupling device has one part of a click fit coupling, and another part of the click fit coupling is part of the fixing element.

15. Apparatus according to claim 12, wherein the coupling device has one part of a pressure and friction coupling and another part of the pressure and friction coupling is a part of the fixing element.

16. Apparatus according to claim 12, wherein the coupling device is one part of a key and lock coupling and another part of the key and lock coupling is part of the fixing element.

17. Apparatus according to claim 5, wherein the hollow closed end needle is provided with a needle indicator.

18. Apparatus according to claim 5, wherein the fixing element comprises a tape adhereable to an animal body and wherein the tape is provided with a needle indicator.

19. Apparatus according to claim 4, wherein the flexible closed end sheath is at least in part collapsible under pressures present on the channel in a body.

20. Apparatus according to claim 19, wherein a part near or at a distal end of the flexible closed end sheath is not substantially collapsible under pressures present on the channel in a body.

21. Apparatus according to claim 20, wherein a radiopaque marker is present in said not substantially collapsible part of said flexible closed end sheath.

22. Apparatus according to claim 4, wherein a radiopaque marker is present in a distal end of said flexible closed end sheath.

23. Apparatus according to claim 4, wherein the flexible closed end sheath is of a heat meltable material and the heat melted flexible closed end sheath adheres to the fixing element upon cooling in contact therewith.

24. Apparatus according to claim 4, wherein the connecting element is for detachably connecting the radioactive device to the fixing element.

* * * * *